United States Patent [19]
Langworth

[11] Patent Number: 6,013,246
[45] Date of Patent: Jan. 11, 2000

[54] PREPARATION FOR INHIBITING THE RELEASE OF MERCURY AND FOR RENDERING MERCURY RELEASED FROM AMALGAM FILLINGS HARMLESS

[75] Inventor: Sven Langworth, Enebyberg, Sweden

[73] Assignee: CTC Medical AB, Stockholm, Sweden

[21] Appl. No.: 08/696,964

[22] PCT Filed: Feb. 28, 1995

[86] PCT No.: PCT/SE95/00207

§ 371 Date: Aug. 23, 1996

§ 102(e) Date: Aug. 23, 1996

[87] PCT Pub. No.: WO95/23584

PCT Pub. Date: Sep. 8, 1995

[30] Foreign Application Priority Data

Mar. 2, 1994 [SE] Sweden .................................. 9400714

[51] Int. Cl.$^7$ ...................................................... A61K 7/16
[52] U.S. Cl. .............................. 424/49; 424/56; 433/226; 433/228.1
[58] Field of Search ................................. 433/226, 228.1; 424/49, 56

[56] References Cited

U.S. PATENT DOCUMENTS

| | | | |
|---|---|---|---|
| 3,303,173 | 2/1967 | Wandeler et al. | 260/79.7 |
| 4,486,403 | 12/1984 | Mechanic et al. | 424/54 |
| 4,590,067 | 5/1986 | Meisner | 424/54 |
| 5,100,653 | 3/1992 | Campo | 424/54 |
| 5,178,541 | 1/1993 | Goodman | 433/226 |
| 5,182,099 | 1/1993 | Jonsson et al. | 424/49 |

OTHER PUBLICATIONS

Twardowska–Saucha, Krystyna, "Evaluation of the chelating action of methicillin in prolonged experimental metallic mercurry poisoning", *Chemical Abstracts*, vol. 105, No. 21, col. 2, Nov. 1986, p. 215.

Twardowska–Saucha, K. of CA(105)21:185439c, Nov. 1986.

Dudman et al., "Homocysteine thiolactone and experimental homocysteinemia", Biochem. Med. 27(2), pp. 244–253, see abstract, 1982.

Butler et al., "The pentacyanonitosylferrate ion V. The course of the reactions of nitroprusside with a range of thiols", Polyhedron (1988), 7(13), pp. 1197–1202, 1988.

Kasuya, M., "Effect of inorganic, aryl, alkyl, and other mercury compounds on the outgrowth of cells and fibers from dorsal root ganglia in tissue culture", Toxicol. Appl. Pharmacol. 23(1), 136–146, 1972.

*Primary Examiner*—Dwayne C. Jones
*Attorney, Agent, or Firm*—Young & Thompson

[57] ABSTRACT

A preparation for inhibiting the release of mercury or to render mercury that is released when treating amalgam dental fillings or when inserting new amalgam fillings, harmless. The preparation contains at least 0.01 percent by weight of a physiologically acceptable organic sulphur compound, which includes at least one group chosen from SH and $R_1$-$S_n$-$R_2$, where n=1--6. The use of such a preparation in mouth washes, mouth sprays, toothpastes, dental prophylactic pastes or rinsing/cooling liquids intended for use when drilling, abrading, polishing or cleaning with the aid of dental instruments. A therapeutic treatment preparation may include cysteine for rendering Hg harmless in solution form and/or gas form in the oral cavities of human beings and animals.

8 Claims, 1 Drawing Sheet

PREPARATION FOR INHIBITING THE RELEASE OF MERCURY AND FOR RENDERING MERCURY RELEASED FROM AMALGAM FILLINGS HARMLESS

This application is a 371 of PCT/SE95/00207, filed on Feb. 28, 1995.

FIELD OF THE INVENTION

The present invention relates to a preparation for inhibiting the release of mercury (Hg) from amalgam and/or rendering mercury, that is released when treating existing dental amalgam fillings and/or when inserting new amalgam fillings, harmless. The preparation is intended for clinical use, i.e. by dental personnel such as dentists and dental nurses for instance, and also by people whose teeth include amalgam fillings. The preparation can also be used on animals. The invention also relates to the use of such a preparation.

BACKGROUND OF THE INVENTION

Mercury is a heavy metal whose toxic effect is well known. Amalgams are alloys which contain relatively large quantities of Hg. Amalgam used in dental fillings contains about 50 percent by weight metallic Hg. Hg is released more or less continuously from the fillings in both vapor form and in the form of solution, as a result of the corrosion and the wear that occurs naturally in the oral cavity because of the abrasion between fillings and tooth surfaces, and also as a result of the pH of the saliva. The amount of Hg released will increase when the fillings are subjected to pronounced strain, particularly when chewing, for instance in conjunction with consuming different foodstuffs, and also when brushing the teeth, and may be more than 6-fold in cases such as these. This elevated Hg release will often not diminish until 40–50 minutes have lapsed after termination of this pronounced strain on the fillings. Mercury that is released in vapor form and in the form of a solution is taken up via the lungs or swallowed with saliva. Investigations have shown that the average daily absorption of mercury per person is about 3 –17 $\mu$g ("Inorganic mercury", Environmental Health Criteria Document 118, WHO 1991). Although there is some controversy as to whether or not the ingestion of such quantities would regularly result in Hg-poisoning, there is no doubt that comparatively highly sensitive persons can be afflicted by these mercury levels. Dental personnel handling amalgam are also exposed to the mercury that is released during treatment, particularly when inserting new fillings and when polishing and drilling existing fillings. It has been found that on such occasions, the ambient air can have mercury concentration values as high as 50 $\mu$g/m$^3$ measured in the breathing zone (Langworth, S., et al. "Undersökningar av kvicksilverexponering och hälsorisker förknippade med amalgamhantering"; Slutrapport Arbetsmiljöfonden, 1989). These high levels can be compared with the professional hygienic level limit currently applied in Sweden, which is only 30 $\mu$g/m$^3$.

SE-B-463 189 describes a preparation for introduction into the oral cavity. The purpose of this preparation is to prevent the release of Hg and Hg vapor from dental amalgam fillings or to reduce reduce the extent of such release. The preparation contains sulphur in a free form, preferably in concentrations of 0.1 –0.01 percent by weight and in particle sizes in the range of 0.05 –0.01 mm. Although it is maintained in the patent specification that the preparation may be present in many different forms, the sole embodiments described with examples are toothpaste and chewing gum, wherein the sulphur grains have an average size of 0.025 mm. In the examples documented, the sulphur is present in concentrations of 0.005 –5 percent by weight. However, it is also anticipated that the preparation may be used in mouth washes, mouth sprays, abrading and polishing agents and as a coolant when using dental instruments. This would create considerable problems in practice, however. For instance, it is highly unlikely that a colloidal sulphur solution could be used in dental instrument washing liquids without the sulphur particles settling to form a sediment, with the subsequent risk of clogging valves and like devices. A corresponding clogging risk would also be likely in the case of a mouth spray. The use of colloidal sulphur in a mouth-washing agent would also appear impractical in view of the unavoidable sedimentation risk.

U.S. Pat No. 5,178,541 also describes preparations and methods for preventing release of Hg and Hg vapor. This document also discloses the use of sulphur in such preparations and methods. A protective layer may be formed over hardened amalgam surfaces by brushing with a toothpaste composition containing sulfur. Alternatively, surfaces of a tooth cavity can be coated with a lining composition containing sulfur before inserting the dental amalgam. Also, sulphur may be incorporated into setting compositions comprising a dental amalgam alloy. Nothing is disclosed about preparations that can be used when polishing and drilling existing fillings.

WO 88/05295 describes a composition which is intended to prevent poisoning as a result of the dissolution of Hg from amalgam fillings, this composition containing selenium iodide. Selenium compounds, however, are known to be highly toxic, a problem which can hardly be ignored in the present context.

Chemical Abstracts, Vol. 105, abstract number 185439c & Twardowska-Saucha: Br. J. Ind. Med. 1986, 43(9), 611 –14, discloses treatment of mercury poisoning of animals with methicillin or penicillamine. Nothing is revealed about any dental applications.

Thus, there exists a need for means which are effective in inhibiting the release of Hg and in rendering released Hg harmless and which are not encumbered with the aforesaid problems.

SUMMARY OF THE INVENTION

Such means have now been produced in the form of preparations of the kind defined in the introduction, these preparations being characterized by including at least 0.01 percent by weight, calculated on the total on the total weight of the preparation, of at least one physiologically acceptable organic sulphur compound which includes at least one group chosen between SH and R$_1$–S$_n$–R$_2$, wherein n =1 –6, and R$_1$ and R$_2$ are organic groups.

In addition to solving the aforesaid problems, tests carried on these preparations were found to provide surprisingly good results in comparison with the known technique.

According to one embodiment of the present invention, the preparations contain sulphur organic compounds, for instance thiols, thiocarboxylic acids or thioaldehydes. Specific examples of sulphur organic compounds are thiocarbamide, dithiodiethanol, 2,3-dimercaptobutanedioic acid, 2-mercaptobutanedioic acid, 2,3-dimercapto-1-propanol and derivatives thereof.

According to one preferred embodiment, the sulphur organic compound is an amino acid, for instance cysteine, homocysteine, acetylcysteine, cystine, penicillamine, glutathione, methionine or a derivative thereof, an amino acid-hydrochloride or a protein, for instance an albumin.

According to one particularly preferred embodiment, the sulphur organic compound is cysteine.

The compound is present in the inventive preparations in amounts corresponding to up to 10 percent by weight, preferably up to 5 percent by weight, and particularly up to 1 percent by weight, wherein the remainder of the preparation is comprised of up to 100 percent by weight of a physiologically acceptable extender or an agent, such as a solvent, for instance, in which the compound is dissolvable at the concentration concerned, preferably water, and possibly other conventional additives for the use in question, such as abrasive agents, flavorants, thickeners, etc.

In one particularly preferred embodiment, the preparation includes 0.1 –5 percent by weight cysteine.

According to another embodiment of the present invention, the aforedescribed preparation is used in mouthwashes, toothpaste, tooth prophylactic paste or in rinsing and/or cooling liquid intended for use when drilling, abrading, polishing or cleaning teeth with the aid of dental instruments.

In another embodiment of the present invention, cysteine is used in the production of a preparation for therapeutical treatment in the oral cavity of human-beings or animals with the intention of rendering harmless Hg in a dissolved and/or gaseous state.

One feasible explanation for the effectiveness of the preparations is that from a steric aspect, the Sn groups and SH groups of the compounds present in the preparations are able to react with Hg atoms and Hg ions relatively unhindered. It is also feasible that the groups in question are caused to react with the amalgam fillings through the medium of a sorption process, wherein not-readily dissolved compounds are formed, and steric hinderance against the release of unreacted Hg atoms is obtained.

BRIEF DESCRIPTION OF THE DRAWINGS

The present invention will now be illustrated with the aid of examples and with reference to the accompanying drawings, in which.

DESCRIPTION OF THE PREFERRED EMBODIMENTS

Intraoral Hg concentration after brushing the teeth, with and without subsequent treatment

Comparison Example I

Figure 1:
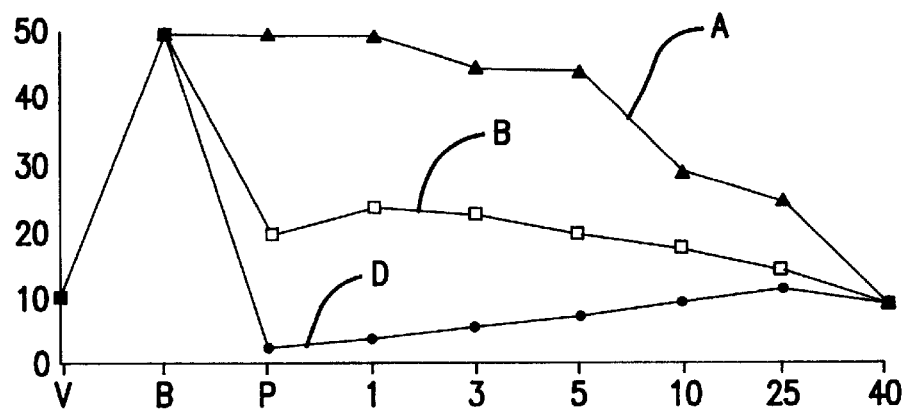
FIG. 1 is a diagram which illustrates intraoral Hg concentration (plotted on the y-axis with the unit $\mu g/m^3$) after brushing the teeth and partly without and partly with subsequent rinsing with water (curve A) and aqueous solutions of colloidal sulphur (5%) (curve B) and cysteine (2%) (curve D) respectively as a function of time (measured in minutes)

In one test, the concentration of mercury in the air in the oral cavity of a test person having about 15 amalgam dental fillings was measured with the aid of a single-beam atom absorption spectrophotometer manufactured by Centrum för Dental Bioteknik (CDB), Novum, Huddinge, Sweden, which had been calibrated against a newly calibrated gold film instrument designated "JEROME 411"(marketed by Jerome Corporation, U.S.A.), which is intended for measuring the concentration of air-borne Hg vapor. The first measuring process was carried out after the amalgam fillings had been at rest for two hours, which in the present context implies that the fillings had not been subjected to any particular form of strain, such as brushing, chewing or the like over this period. Upon completion of this measuring process, the fillings were subjected to wear, or abrasion) by brushing the teeth with a conventional toothpaste that contained an abrasive (fluorine-containing toothpaste bearing the trademark COLGATE®), whereafter the mouth was rinsed with water. After having rinsed the mouth, the Hg concentration was measured for a second time. A pronounced increase in Hg concentration was established, as evident from Table 1 below and from FIG. 1. Prevailing Hg concentrations in the oral cavity air were then measured after 1, 3, 5, 10, 25 and 40 minutes respectively, at which latter time the Hg concentration had returned essentially to its original value. The results of these measurements are noted in column A of Table 1 below, and also with the aid of curve A in FIG. 1.

Comparison Example II

The test of Comparison Example I was repeated, with the exception that the mouth was washed out immediately after brushing the teeth, followed by rinsing with a colloidal aqueous solution containing 5 percent by weight of sulphur, calculated on the total weight of the solution, having a particle size of up to about 12 $\mu$m (marketed by Fluka Chemie AG, Buchs, Switzerland).

The Hg concentration in the oral cavity air was measured partly when the fillings had been at rest for two hours (according to the definition in Comparison Example I), and partly in conjunction with brushing the teeth and the subsequent rinsing of the mouth, and 1, 3, 5, 10, 25 and 40 minutes respectively after rinsing the mouth. The results obtained with these measuring processes are noted in column B in Table 1 below and also with the aid of curve B in FIG. 1.

Comparison Example III

The test of Comparison Example II was repeated, but with the exception that the mouth was rinsed with a colloidal aqueous solution containing 2 percent by weight sulphur, calculated on the total weight of the solution. The Hg concentration of the oral cavity air was measured in the same way as in Comparison Example II. The results obtained from these measuring processes are noted in column C in Table 1 below.

EXAMPLE 1

The test of Comparison Example II was repeated, but with the exception that the mouth was rinsed with an aqueous solution that contained 2 percent by weight cysteine, calculated on the total weight of the solution. The Hg concentration in the oral cavity air was measured in the same way as that in Comparison Example II. The results of these measuring processes are noted in column D in Table 1 below and also with the aid of curve D in FIG. 1.

EXAMPLE 2

The test carried out in Comparison Example II was repeated, but with the exception that the mouth was rinsed with an aqueous solution that contained 2 percent by weight homocysteine, calculated on the total weight of the solution. The Hg concentration in the oral cavity air was measured in the same way as in Comparison Example II. The results of these measuring processes are noted in column E in Table 1 below.

EXAMPLE 3

The test carried out in Comparison Example II was repeated, but with the exception that the mouth was washed with an aqueous solution containing 2 percent by weight of acetylcystein, calculated on the total weight of the solution. The Hg concentration in the oral cavity air was measured in the same way as in Comparison Example II. The results of these measuring processes are noted in column F in Table 1 below.

EXAMPLE 4

The test carried out in Comparison Example II was repeated, but with the exception that the mouth was rinsed with an aqueous solution that contained 2 percent by weight of 2,3-dimercaptobutanedioic acid, calculated on the total weight of the solution. The Hg concentration in the oral cavity air was measured in the same way as in Comparison Example II. The results of these measuring processes are noted in column G in Table 1 below.

EXAMPLE 5

The test carried out in Comparison Example II was repeated, but with the exception that the mouth was rinsed with an aqueous solution that contained 2 percent by weight of 2-mercaptobutane-dioic acid, calculated on the total weight of the solution. The Hg concentration in the oral cavity air was measured in the same way as in Comparison Example II. The results of these measuring processes are noted in column H in Table 1 below.

EXAMPLE 6

The test carried out in Comparison Example II was repeated, but with the exception that the mouth was rinsed with an aqueous solution that contained 2 percent by weight penicillamine, calculated on the total weight of the solution. The Hg concentration in the oral cavity air was measured in the same way as in Comparison Example II. The results of these measuring processes are noted in column I in Table 1 below.

EXAMPLE 7

The test carried out in Comparison Example II was repeated, but with the exception that the mouth was washed with an aqueous solution containing 2 percent by weight human standard albumin, calculated in the total weight of the solution (marketed in a 0.85% NaCl solution by Sigma, St. Louis, Missouri, U.S.A.). The Hg concentration in the oral cavity air was measured in the same way as in Comparison Example II. The results of these measuring processes are noted in column K in Table 1 below.

EXAMPLE 8

The test carried out in Comparison Example II was repeated, but with the exception that the mouth was washed with an aqueous solution containing 2 percent by weight of glutathione, calculated on the total weight of the solution. The Hg concentration in the oral cavity air was measured in the same way as in Comparison Example II. The results of these measuring processes are noted in column L in Table 1 below.

EXAMPLE 9

The test carried out in Comparison Example II was repeated, but with the exception that the mouth was washed with an aqueous solution containing 2 percent by weight 2,3-dimercapto-l-pro-panol, calculated on the total weight of the solution. The Hg concentration in the oral cavity air was measured in the same way as in Comparison Example II. The results of these measuring processes are noted in column M in Table 1 below.

As will be seen from Table 1, all of the solutions used in the Examples had a positive effect with regard to the Hg concentration in the oral cavity air during the first five minutes after treatment. Surprisingly, cysteine, homocysteine, 2-3-dimercapto-1-propanol and 2,3-dimercaptobutandioic acid in 2% aqueous solution gave much better results than a colloidal aqueous sulphur solution, even a 5% solution. A separate comparison between the measuring results obtained in comparison Examples I and II and Example 1 is shown in the diagram in FIG. 1, in which the Hg concentration is plotted on the y-axis in $\mu g/m^3$ and the time is plotted on the x-axis in minutes. This comparison clearly shows that a cysteine solution is much more effective than a colloidal sulphur solution for the purpose in question.

TABLE 1

Intraoral Hg concentration in oral cavity air after brushing the teeth and subsequent rinsing, measured in $\mu g/m^3$

| Time | A | B | C | D | E | F | G | H | I | K | L | M |
|---|---|---|---|---|---|---|---|---|---|---|---|---|
| Rest ("V" in FIG. 1) | 10 | 10 | 10 | 10 | 10 | 10 | 10 | 10 | 10 | 10 | 10 | 10 |
| After brushing/washing ("X" in FIG. 1) | 50 | 50 | 50 | 50 | 50 | 50 | 50 | 50 | 50 | 50 | 50 | 50 |
| After mouth washing ("p" in FIG. 1) | 50 | 20 | 22 | 3 | 4 | 12 | 6 | 10 | 30 | 40 | 15 | 3 |
| 1 min | 50 | 24 | 26 | 4 | 6 | 14 | 8 | 12 | 33 | 35 | 14 | |
| 3 min | 45 | 23 | 24 | 6 | 10 | 17 | 8 | 11 | 35 | 35 | 16 | 2 |
| 5 min | 45 | 20 | 22 | 8 | 12 | 16 | 10 | 11 | 35 | 35 | 20 | 3 |
| 10 min | 30 | 18 | 20 | 10 | 12 | 18 | 12 | 12 | 34 | 30 | 20 | 5 |
| 25 min | 25 | 15 | 16 | 12 | 11 | 16 | 10 | 15 | 30 | 25 | 16 | 8 |
| 40 min | 10 | 10 | 10 | 10 | 10 | 12 | 10 | 12 | 12 | 12 | 10 | 12 |

Intraoral Hg concentration when drilling amalgam fillings and with and without simultaneous rinsing/cooling with different aqueous solutions

Comparison Example IV

In one test, the Hg concentration of the air was measured 10 cm above an amalgam filling in a plaster model of a toothed jaw, on which drilling work was performed. The drilling and measuring processes had a duration of 20 seconds. The Hg concentration was measured with the same equipment and in accordance with the same calibration as in Comparison Example I. The measuring results obtained immediately prior to drilling (i.e. at 0 seconds) and at 5, 10, 15 and 20 seconds respectively after commencing drilling are noted in column N in Table 2 below, and with the aid of curve N in FIG. 2.

Comparison Example V

The test carried out in Comparison Example IV was repeated, but with the exception that drilling was carried out while cooling with the aid of a cooling water spray and an air spray (i.e. comparable with conventional water cooling in conjunction with dental work). The Hg concentration in the air was measured in the same way as in Comparison Example IV. The results of these measuring processes are noted in column O in Table 2 below, and with the aid of curve O in FIG. 2.

Comparison Example VI

The test carried out in Comparison Example IV was repeated, but with the exception that drilling was carried out while cooling with the aid of a sprayed-on cooling water solution containing a sulphur slurry in an amount corresponding to about 1 percent by weight calculated on the total weight of the solution. The Hg concentration in the air was measured in the same way as in Comparison Example IV. The results of these measuring processes are noted in column P in Table 2 below, and with the aid of curve P in FIG. 2.

Comparison Example VII

The test carried out in Comparison Example IV was repeated, but with the exception that drilling was performed while cooling with the aid of a sprayed-on cooling water solution containing colloidal sulphur in an amount corresponding to 5 percent by weight calculated on the total weight of the solution. The Hg concentration in the air was measured in the same way as in Comparison Example IV. The results of these measuring processes are noted in column Q in Table 2 below, and with the aid of curve Q in FIG. 3.

Comparison Example VIII

The test carried out in Comparison Example IV was repeated, but with the exception that drilling was performed while cooling with the aid of a sprayed-on cooling water solution containing colloidal sulphur in an amount corresponding to 1 percent by weight of the total weight of the solution. The Hg concentration in the air was measured in the same way as in Comparison Example IV. The results of these measuring processes are noted in column R in Table 2 below, and with the aid of curve R1 in FIG. 2 and with the aid of curve R2 in FIG. 3.

EXAMPLE 10

The test in Comparison Example IV was repeated, but with the exception that drilling was performed while cooling with the aid of a sprayed-on cooling water solution containing cysteine in amount corresponding to 1 percent by weight calculated on the total weight of the solution. The Hg concentration in the air was measured in the same way as in Comparison Example IV. The results of these measuring processes are noted in column S in Table 2 below, and with the aid of curve S1 in FIG. 2 and with the aid of curve S2 in FIG. 3.

TABLE 2

Intraoral Hg concentration in oral cavity air when drilling amalgam fillings with and without rinsing/cooling with the aid of different aqueous solutions, measured in $\mu g/m^3$

| Time | M | O | P | Q | R | S |
|------|-----|----|----|---|----|---|
| 0 s  | 2   | 2  | 2  | 4 | 2  | 2 |
| 5 s  | 140 | 25 | 20 | 5 | 8  | 2 |
| 10 s | 150 | 40 | 30 | 7 | 10 | 4 |
| 15 s | 250 | 50 | 45 | 8 | 12 | 2 |
| 20 s | 200 | 45 | 40 | 7 | 12 | 3 |

Figure 2:
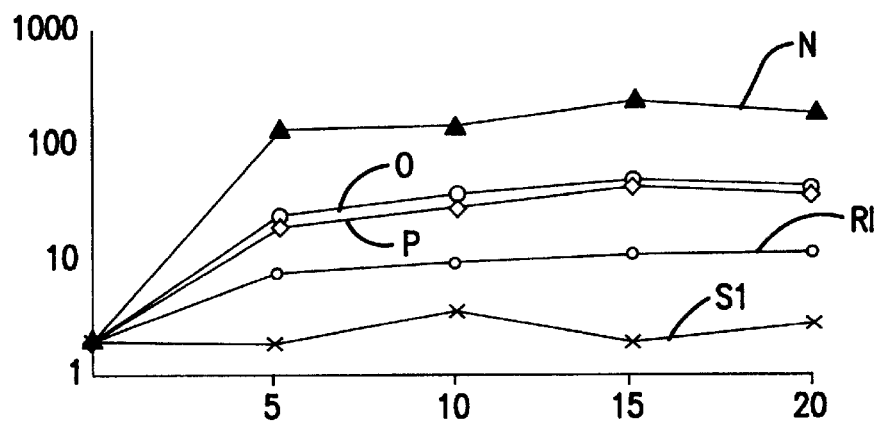
FIG. 2 is a diagram which illustrates air-borne Hg concentrations (the y-axis, $\mu g/m^3$, logarithmic scale) at 10 cm above an amalgam filling when drilling the filling, partly without (curve N) and partly with rinsing/cooling with water (curve O) and with aqueous solutions of sulphur (about 1%) (curve P), colloidal sulphur (1%) (curve Rl) and cysteine (1%) (curve Sl) respectively as a function of time (measured in seconds)
Figure 3:
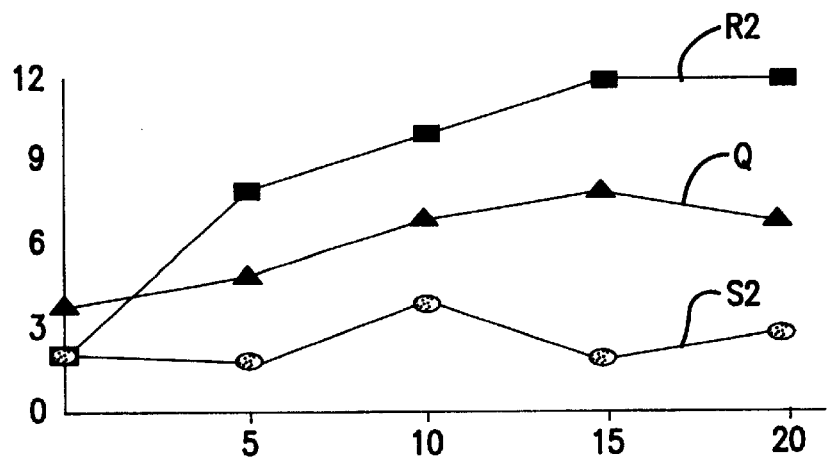
FIG. 3 is a diagram which illustrates an Hg concentration ($\mu g/m^3$) under the same conditions as those for FIG. 2 (although the scale for the Hg concentration is linear in this case), in which only comparisons were made, however, between the effect of aqueous solutions of colloidal sulphur (1 (curve R2) and 5% (curve Q) respectively) and cysteine (1%) (curve S2).

It is clearly apparent from Table 2 and from FIGS. 2 and 3 that a 2% aqueous solution of cysteine is much more effective than a colloidal sulphur solution or a sulphur slurry, even a 5% solution or slurry, with regard to rendering Hg harmless in the oral cavity.

It will be understood that the invention is not restricted to the application described by way of demonstration in the above Examples and that there are many more ways of administering the inventive preparation that will be found natural by one skilled in this art.

I claim:

1. A method of rendering Hg in solution and/or gas form harmless in oral cavities, said method comprising the steps of:

administering to an amalgam dental filling for an oral cavity a preparation including at least one compound selected from the group consisting of an amino acid; a protein; thiocarbamide; dithioethanol; 2,3-dimercaptobutanedioic acid; 2-mercaptobutanedioic acid; and 2,3-dimercapto-1-propanol;

wherein the preparation is free of colloidal sulphur.

2. The method according to claim 1, wherein the amino acid is selected from the group consisting of cysteine, homocysteine, acetylcysteine, cystine, penicillamine, glutathione, methionine and derivatives thereof.

3. The method according to claim 1, wherein the protein is albumin.

4. A composition for inhibiting release of mercury from an amalgam dental filling and/or rendering the mercury that is released in the air or in the mouth of a patient when treating an amalgam dental filling in a tooth and/or when inserting a new amalgam dental filling, harmless, said composition comprising:

an aqueous solution comprising at least 0.01 percent by weight of at least one physiologically acceptable organic sulfur compound selected from the group consisting of thiocarbamide; dithioethanol; 2,3-dimercaptobutanedioic acid; 2-mercaptobutanedioic acid; and 2,3-dimercapto-1-propanol; and a physiologically acceptable oral agent.

5. The composition according to claim 4, wherein the composition includes up to 10 percent by weight of the organic sulfur compound.

6. The composition according to claim 5, wherein the composition includes up to 1 percent by weight of the organic sulfur compound.

7. The composition according to claim 4, wherein the composition includes up to 5 percent by weight of the organic sulfur compound.

8. A method of making a composition for rendering Hg in solution and/or gas form harmless in oral cavities, said method comprising the steps of:

formulating a composition including at least 0.01 percent by weight of at least one physiologically acceptable organic sulfur compound selected from the group consisting of thiocarbamide; dithioethanol; 2,3-dimercaptobutanedioic acid; 2-mercaptobutanedioic acid; and 2,3-dimercapto-1-propanol wherein said formulating step includes embodying the composition in a physiologically acceptable oral agent.

* * * * *